United States Patent
Dong

(10) Patent No.: US 7,993,883 B2
(45) Date of Patent: *Aug. 9, 2011

(54) COMPLEXITY MANAGEMENT OF GENOMIC DNA

(75) Inventor: Shoulian Dong, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,896

(22) Filed: Jun. 24, 2010

(65) Prior Publication Data

US 2010/0292097 A1 Nov. 18, 2010

Related U.S. Application Data

(60) Division of application No. 11/256,505, filed on Oct. 21, 2005, now Pat. No. 7,745,178, which is a division of application No. 09/920,491, filed on Jul. 31, 2001, now Pat. No. 6,958,225, which is a continuation-in-part of application No. 09/428,350, filed on Oct. 27, 1999, now Pat. No. 6,361,947.

(51) Int. Cl.
| | |
|---|---|
| C12P 19/34 | (2006.01) |
| C12Q 1/68 | (2006.01) |
| C07H 21/02 | (2006.01) |
| C07H 21/04 | (2006.01) |
| C07H 21/00 | (2006.01) |

(52) U.S. Cl. ......... 435/91.2; 435/6; 435/91.1; 536/23.1; 536/24.3; 536/24.33; 536/25.3

(58) Field of Classification Search ............. 435/6, 91.1, 435/91.2, 183; 436/94, 501; 536/23.1, 24.3, 536/24.33, 25.3

See application file for complete search history.

(56) References Cited

U.S. PATENT DOCUMENTS

| 4,683,195 A | 7/1987 | Mullis et al. |
|---|---|---|
| 4,683,202 A | 7/1987 | Mullis |
| 4,800,159 A | 1/1989 | Mullis et al. |
| 5,093,245 A | 3/1992 | Keith et al. |
| 5,366,877 A | 11/1994 | Keith |
| 5,508,178 A | 4/1996 | Rose et al. |

(Continued)

FOREIGN PATENT DOCUMENTS

| EP | 534858 B1 | 9/1992 |
|---|---|---|
| WO | WO 00/18960 | 4/2000 |
| WO | WO 01/75163 | 10/2001 |
| WO | WO 02/20844 | 3/2002 |

OTHER PUBLICATIONS

Taqman assay from Wikipedia, the free encyclopedia. Printed on Sep. 28, 2010.*

(Continued)

*Primary Examiner* — Frank W Lu
(74) *Attorney, Agent, or Firm* — Sandra E. Wells

(57) ABSTRACT

The presently claimed invention provides for novel methods and kits for reducing the complexity of a nucleic acid sample by providing non-gel based methods for amplification of a subset of the sequences in a sample. In a preferred embodiment, amplification of a subset can be accomplished by digesting a sample with two or more restriction enzymes and ligating adaptors to the fragments so that only a subset of the fragments can be amplified. The invention further provides for analysis of the above amplified sample by hybridization to an array, which may be specifically designed to interrogate the desired fragments for particular characteristics, such as, for example, the presence or absence of a polymorphism.

2 Claims, 4 Drawing Sheets

U.S. PATENT DOCUMENTS

| | | | |
|---|---|---|---|
| 5,807,522 A | 9/1998 | Brown et al. | |
| 5,858,656 A | 1/1999 | Deugau et al. | |
| 5,888,737 A | 3/1999 | DuBridge et al. | |
| 6,004,783 A | 12/1999 | Ausubel et al. | |
| 6,045,994 A | 4/2000 | Zabeau et al. | |
| 6,100,030 A | 8/2000 | McCasky Feazel et al. | |
| 6,124,090 A | 9/2000 | Rose et al. | |
| 6,156,502 A | 12/2000 | Beattie | |
| 6,197,557 B1 | 3/2001 | Makarov et al. | |
| 6,232,067 B1 | 5/2001 | Hunkapiller et al. | |
| 6,238,884 B1 | 5/2001 | Short et al. | |
| 6,287,825 B1 | 9/2001 | Weissman et al. | |
| 6,472,185 B2 | 10/2002 | McCasky Feazel et al. | |
| 6,514,768 B1 | 2/2003 | Guire et al. | |
| 6,632,611 B2 | 10/2003 | Su et al. | |
| 6,958,225 B2 * | 10/2005 | Dong | 435/91.2 |
| 7,745,178 B2 * | 6/2010 | Dong | 435/91.2 |
| 2003/0113737 A1 | 6/2003 | Pedersen | |

OTHER PUBLICATIONS

"Frequencies of Restriction Sites" from the online catalog of New England Biolabs, Inc. this document is available on Jul. 18, 2002. (neb.com).

Lipshutz, et al., BioTechniques 1993):442-47, 1995.

Smith, PCR Methods and Applications 2:21-27, 1992.

Smith, D.R., "Ligation-mediated PCR of Restriction Fragments from Large DNA Molecules", PCR Methods and Applications, 1992, vol. 2., No. 1, pp. 21-27.

Swa I and Pme I product data sheets, from the online catalog of New England Biolabs, Inc. (neb.com) available on Apr. 1, 2000 and Jul. 13, 2000.

Vos et al., "EFLP: A New technique for DNA Fingerprinting," Nucleic Acids Research, 1995, vol. 23 pp. 4407-4414.

* cited by examiner

COMPLEXITY MANAGEMENT OF GENOMIC DNA

RELATED APPLICATIONS

This application is a division of U.S. application Ser. No. 11/256,505, filed Oct. 21, 2005, now U.S. Pat. No. 7,745,178, which is a divisional of U.S. application Ser. No. 09/920,491, filed Jul. 31, 2001, now U.S. Pat. No. 6,958,225, which is a continuation-in part of U.S. application Ser. No. 09/428,350, filed Oct. 27, 1999, now U.S. Pat. No. 6,361,947, issued on Mar. 26, 2002, the entire teachings of which are incorporated herein by reference in their entirety for all purposes.

FIELD OF THE INVENTION

The invention relates to enrichment and amplification of sequences from a nucleic acid sample. In one embodiment, the invention relates to enrichment and amplification of nucleic acids for the purpose of further analysis. The present invention relates to the fields of molecular biology and genetics.

BACKGROUND

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

In the future disease discovery and diagnosis will be increasingly done at the genetic level. There are already many diseases that are known to be associated with specific genetic components. That number will rapidly increase as researchers continue to acquire information about the genetic variation between individuals and to associate genotypic information with phenotypic characteristics.

SUMMARY OF THE INVENTION

The present invention provides for novel methods of sample preparation and analysis comprising managing or reducing the complexity of a nucleic acid sample. The present invention eliminates the need for multiplex PCR and for many of the embodiments the step of complexity reduction may be performed entirely in a single tube. The invention further provides for analysis of the sample by hybridization to an array which may be specifically designed to interrogate fragments for particular characteristics, such as, for example, the presence or absence of a polymorphism. The invention further provides for methods of using a computer system to model enzymatic reactions in order to determine experimental conditions and to design arrays. In a preferred embodiment the invention discloses novel methods of genome-wide polymorphism discovery and genotyping.

In one embodiment the present invention provides methods for reducing the complexity of a nucleic acid sample by fragmenting the nucleic acid sample using restriction enzymes; ligating adaptors to the fragments; and selectively amplifying the fragments that were cut on one end by one restriction enzyme and on the other end by a different restriction enzyme. The complexity of the resulting sample can be regulated by choosing enzymes that cut with a particular frequency.

In one embodiment of the current invention selective amplification is accomplished by blocking ligation of one strand of each adaptor so that fragments that have the same adaptor ligated to both ends will have gaps in both strands but fragments that have one adaptor ligated to one end and a second adaptor ligated to the other end will have one complete strand for amplification. In this embodiment, ligation is blocked at the 5' end of one adaptor and at the 3' end of the other adaptor.

In another embodiment of the current invention selective amplification is accomplished by designing one adaptor to have a 5' overhang and the second adaptor to have a 3' overhang. The overhangs comprise primer binding sites.

Many of the embodiments of the current invention can further reduce complexity by designing the primers for amplification to bind to one or more nucleotides of the variable region of the restriction fragments.

In yet another embodiment, the invention relates to a kit comprising reagents and instructions for reducing the complexity of a nucleic acid sample. The kit may comprise buffers, restriction enzymes, adaptors, primers, a ligase, a polymerase, dNTPS and instructions necessary for use of the kit.

The present invention also provides methods for genotyping an individual which may further comprise contacting the amplified sequences with a solid support comprising nucleic acid probes, and detecting the presence or absence of hybridization of the amplified sequences to the nucleic acid probes on the solid support. The immobilized probes in a preferred embodiment are capable of interrogating one or more polymorphic sites. The identity of the polymorphic base is determined from the hybridization information.

DETAILED DESCRIPTION

(A) General

Figure 1:
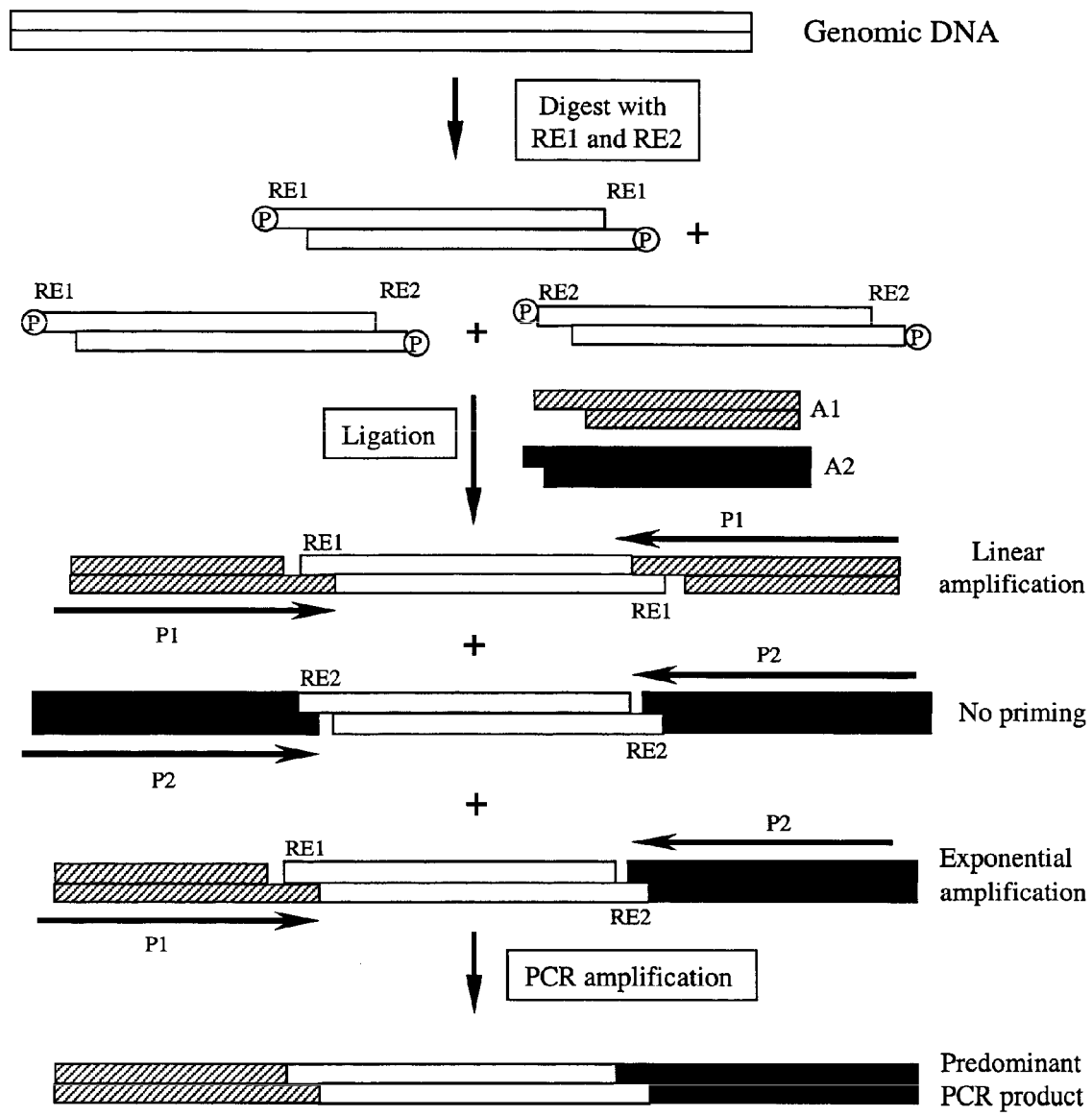
FIG. 1 is a schematic illustration of a method of complexity reduction that uses targeted amplification of a subset of restriction fragments wherein the targeting is accomplished by selectively blocking ligation of one strand of each of two adaptors.

The present invention provides a flexible and scalable method for analyzing complex samples of nucleic acids, such as genomic DNA. These methods are not limited to any particular type of nucleic acid sample: plant, bacterial, animal (including human) total genome DNA, RNA, cDNA and the like may be analyzed using some or all of the methods disclosed in this invention. The word "DNA" may be used below as an example of a nucleic acid. It is understood that this term includes all nucleic acids, such as DNA and RNA, unless a use below requires a specific type of nucleic acid. This invention provides a powerful tool for analysis of complex nucleic acid samples. From experimental design to isolation of desired fragments and hybridization to an appropriate array, the invention provides for fast, efficient and inexpensive methods of complex nucleic acid analysis.

The present invention relies on many patents, applications and other references for details known to those of the art. Therefore, when a patent, application, or other reference is cited or repeated below, it should be understood that it is incorporated by reference in its entirety for all purposes as well as for the proposition that is recited. As used in the specification and claims, the singular form "a," "an," and "the" include plural references unless the context clearly dictates otherwise. For example, the term "an agent" includes a plurality of agents, including mixtures thereof. An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as common individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, $10$, $10^{-1}$, $10^{-2}$, $10^{-3}$, $10^{-4}$, or $10^{-5}$, for example. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), all of which are herein incorporated in their entirety by reference for all purposes.

Some aspects of the present invention make use of microarrays, also called arrays. Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555. All of the above patents incorporated herein by reference in their entireties for all purposes.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated by reference in its entirety for all purposes). Indeed, the present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety for all purposes.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "fragment," "segment," or "DNA segment" refers to a portion of a larger DNA polynucleotide or DNA. A polynucleotide, for example, can be broken up, or fragmented into, a plurality of segments. Various methods of fragmenting nucleic acids are well known in the art. These methods may be, for example, either chemical or physical in nature. Chemical fragmentation may include partial degradation with a DNAse; partial depurination with acid; the use of restriction enzymes; intron-encoded endonucleases; DNA-based cleavage methods, such as triplex and hybrid formation methods, that rely on the specific hybridization of a nucleic acid segment to localize a cleaveage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," 3$^{rd}$ Ed. Cold Spring Harbor Laboratory Press, Cold Spring Harbor, N.Y. (2001) ("Sambrook et al.") which is incorporated herein by reference in its entirety for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample. In general, a restriction enzyme recognizes a specific nucleotide sequence of four to eight nucleotides and cuts the DNA at a site within or a specific distance from the recognition sequence. For example, the restriction enzyme EcoRI recognizes the sequence GAATTC and will cut a DNA molecule between the G and the first A. The length of the recognition sequence is roughly proportional to the frequency of occurrence of the site in the genome. A simplistic theoretical estimate is that a six base pair recognition sequence will occur once in every 4096 ($4^6$) base pairs and is considered to be a "rare cutter", while a four base pair recognition sequence will occur once every 256 ($4^4$) base pairs and is considered to be a "frequent cutter". An enzyme with an 8 base pair recognition sequence is also a "rare cutter" cutting once every $4^8$ base pairs. In silico digestions of sequences from the Human Genome Project show that the actual occurrences are even more infrequent, depending on the sequence of the restriction site. Because the restriction sites are rare, the appearance of shorter restriction fragments, for example those less than 1000 base pairs, is much less frequent than the appearance of longer fragments. Many different restriction enzymes are known and appropriate restriction enzymes can be selected for a desired result. (For a description of many restriction enzymes, see New England BioLabs Catalog which is herein incorporated by reference in its entirety for all purposes).

"Adaptor sequences" or "adaptors" are generally oligonucleotides of at least 5, 10, or 15 bases and preferably no more than 50 or 60 bases in length, however, they may be even longer, up to 100 or 200 bases. Adaptor sequences may be synthesized using any methods known to those of skill in the art. For the purposes of this invention they may, as options, comprise templates for PCR primers, restriction sites and promoters. The adaptor may be entirely or substantially double stranded. The adaptor may be phosphorylated or unphosphorylated on one or both strands. Adaptors are particularly useful in one embodiment of the current invention if they comprise short single stranded regions, which are complementary to the single stranded region, also known as an overhang, created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment facilitates ligation of the adaptor to the fragment, although blunt ended ligation is also possible. Different restriction enzymes cleave DNA to produce different overhangs and adaptors can be designed for any overhang. For a list of many restriction enzymes, their recognition sites and the resulting cleavage products, see, for example, New England Biolabs Catalog, which is herein incorporated by reference in its entirety for all purposes, available from the New England Biolabs website.

Digestion with two or more enzymes can be used to selectively ligate separate adaptors to either end of a restriction fragment. Restriction fragments that have been generated by two different restriction enzymes will often have two distinct overhangs. A pair of adaptors can be designed to ligate specifically to one or the other overhang so that the fragment will ligate to one adaptor on one end and to the second adaptor on the other end. For example, if a fragment is the result of digestion with EcoRI at one end and BamHI at the other end, the overhangs will be 5'-AATT-3' and 5'GATC-3', respectively. An adaptor with an overhang of AATT will be preferentially ligated to one end while an adaptor with an overhang of GATC will be preferentially ligated to the second end.

A single adaptor can also be ligated to both ends of a fragment resulting from digestion with two different enzymes. For example, if the method of digestion generates blunt ended fragments, the same adaptor sequence can be ligated to both ends. Alternatively some pairs of enzymes leave identical overhanging sequences. For example, BglII recognizes the sequence 5'-AGATCT-3', cutting after the first A, and BamHI recognizes the sequence 5'-GGATCC-3', cutting after the first G; both leave an overhang of 5'-GATC-3'. A single adaptor with an overhang of 5'-GATC-3' may be ligated to both digestion products. Adaptors can also be designed to recreate the original restriction site, create a new restriction site or to eliminate the original site.

Methods of ligation will be known to those of skill in the art and are described, for example in Sambrook et al. and the New England BioLabs catalog, both of which are incorporated herein in their entireties by reference for all purposes. Methods include using T4 DNA ligase, which catalyzes the formation of a phosphodiester bond between juxtaposed 5' phosphate and 3' hydroxyl termini in duplex DNA or RNA with blunt or and sticky ends; Taq DNA ligase, which catalyzes the formation of a phosphodiester bond between juxtaposed 5' phosphate and 3' hydroxyl termini of two adjacent oligonucleotides that are hybridized to a complementary target DNA; E. coli DNA ligase, which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art.

"Genome" designates or denotes the complete, single-copy set of genetic instructions for an organism as coded into the DNA of the organism. A genome may be multi-chromosomal such that the DNA is distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ by while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term subset or representative subset refers to a fraction of a genome. The subset may be, for example, 0.01, 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

An "array" comprises a support, preferably solid, with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes.

Preferred arrays are commercially available from Affymetrix under the brand name GENECHIP® and are directed to a variety of purposes, including genotyping and gene expression monitoring for a variety of eukaryotic and prokaryotic species. (See Affymetrix Inc., Santa Clara and the Affymetrix website.

Polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in the human population, and are the most common type of human genetic variation. The site is usually preceded by and followed by highly conserved sequences of the allele (e.g., sequences that vary in less than $1/100$ or $1/1000$ members of the populations). It is estimated that there are as many as $3 \times 10^6$ SNPs in the human genome.

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term genotyping refers to the determination of the genetic information an individual carries at one or more positions in the genome. For example, genotyping may comprise the determination of which allele or alleles an individual carries for a single polymorphism or the determination of which allele or alleles an individual carries for a plurality of polymorphisms.

Hybridization probes are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. See U.S. Pat. No. 6,156,501.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al., which is hereby incorporated by reference in its entirety for all purposes above.

An individual is not limited to a human being, but may also include other organisms including but not limited to mammals, plants, bacteria or cells derived from any of the above.

In silico digestion is a computer aided simulation of enzymatic digests accomplished by searching a sequence for restriction sites. In silico digestion provides for the use of a computer system to model enzymatic reactions in order to determine experimental conditions before conducting any actual experiments. An example of an experiment would be to model digestion of the human genome with specific restriction enzymes to predict the sizes of the resulting restriction fragments.

(C.) The Process

The present invention provides for novel methods of sample preparation and analysis involving managing or reducing the complexity of a nucleic acid sample, such as genomic DNA, by amplifying a representative subset of the sample. The invention further provides for analysis of the above subset by hybridization to an array, which may be specifically designed to interrogate the desired fragments for particular characteristics, such as, for example, the presence or absence of a polymorphism. The invention is particularly useful when combined with other methods of genome analysis. As an example, the present techniques are useful to genotype individuals after polymorphisms have been identified.

One method that has been used to isolate a subset of a genome is to separate fragments according to size by electrophoresis in a gel matrix. The region of the gel containing fragments in the desired size range is then excised and the fragments are purified away from the gel matrix. The SNP consortium (TSC) adopted this approach in their efforts to discover single nucleotide polymorphisms (SNPs) in the human genome. See, Altshuler et al., *Science* 407: 513-516 (2000) and The International SNP Map Working Group, *Nature* 409: 928-933 (2001) both of which are herein incorporated by reference in their entirety for all purposes.

The present invention provides methods of complexity management of nucleic acid samples, such as genomic DNA, that can be used as an alternative to separation of fragments by gel electrophoresis and purification of fragments from a gel matrix. Generally, the embodiments include the steps of: fragmenting the nucleic acid by digestion with two or more restriction enzymes; ligating adaptors to the ends of the fragments; and selectively amplifying a subset of the fragments that have a first adaptor ligated to one end and a second, different adaptor ligated to the other end. In a preferred embodiment the amplified sequences are then exposed to an array which may or may not have been specifically designed and manufactured to interrogate the amplified sequences. Design of both the complexity management steps and the arrays may be aided by computer modeling techniques. Generally, the steps of the present invention involve reducing the complexity of a nucleic acid sample using the disclosed techniques alone or in combination.

When interrogating genomes it is often useful to first reduce the complexity of the sample and analyze one or more subsets of the genome. Subsets can be defined by many characteristics of the fragments. In a preferred embodiment of the current invention the subsets are defined by the restriction enzymes used to generate the fragments and the resulting structure of the ends of the fragments. In some embodiments, the subset is further defined by the identity of one or more nucleotides flanking one or both of the restriction enzyme sites used to generate the fragment.

The genomic DNA sample of the current invention may be isolated according to methods known in the art, such as PCR, reverse transcription, and the like. It may be obtained from any biological or environmental source, including plant, animal (including human), bacteria, fungi or algae. Any suitable biological sample can be used for assay of genomic DNA. Convenient suitable samples include whole blood, tissue, semen, saliva, tears, urine, fecal material, sweat, buccal, skin and hair.

In a preferred embodiment of the invention, adaptors are ligated to the ends of the fragments and the fragments are amplified by PCR using primers that are designed to hybridize to sequences in the adaptors. In a particularly preferred embodiment, a single primer pair can be used for amplification.

FIG. 1 depicts a schematic illustration of the general steps of a preferred embodiment of the currently claimed invention. First, a sample of genomic DNA is fragmented with a first restriction enzyme, RE1, which in a preferred embodiment is a rare cutter, and a second restriction enzyme, RE2, which in a preferred embodiment is a frequent cutter, to produce three types of fragments. The most common fragments are those which have been cut on both ends with the frequent base cutter. Those fragments, which have been cut on one end with the frequent base cutter and on one end with the rare base cutter will be less frequent. The least common fragments are those which have been cut on both ends with the rare base cutter. One of the adaptors, A1, is designed to ligate to the overhang left by the rare cutter and the other adapter, A2, is designed to ligate to the overhang left by the frequent cutter. Fragments that are cut twice by RE1 will ligate to adaptor A1 on both ends. Fragments that are cut twice by RE2 will ligate to adaptor A2 on both ends. Those fragments that have been cut once with RE1 and once with RE2 will ligate to adaptor A1 on one end and to adaptor A2 on the other end. The adaptors further comprise a primer binding site.

In the embodiment of the invention illustrated in FIG. 1, ligation of one strand of each adapter is blocked. Blocking ligation of one strand of the adaptor to the fragments results in a gap or nick between that strand and one strand of the fragment. The gap or nick will block primer extension. In the current invention, one adaptor is designed so that ligation is blocked between the 3' end of one strand of the adaptor and the 5' end of the fragment and the other adaptor is designed to block ligation between the 5' end of one strand of the adaptor and the 3' end of the fragment.

After adaptor ligation the sample is amplified by PCR. Primer P1, specific for adaptor A1, and primer P2, specific for adapter A2, are added, and the mixture is used as template for PCR. Fragments with two identical adaptors are not amplified because primer extension is blocked in both strands at the introduced gaps or nicks (see, FIG. 2) so the first strand of DNA synthesized terminates without the primer binding site needed for second strand synthesis. However, fragments with both adaptors A1 and A2 will be amplified because both introduced gaps or nicks are in the same strand leaving a complete strand to serve as a template for PCR.

Figure 2:
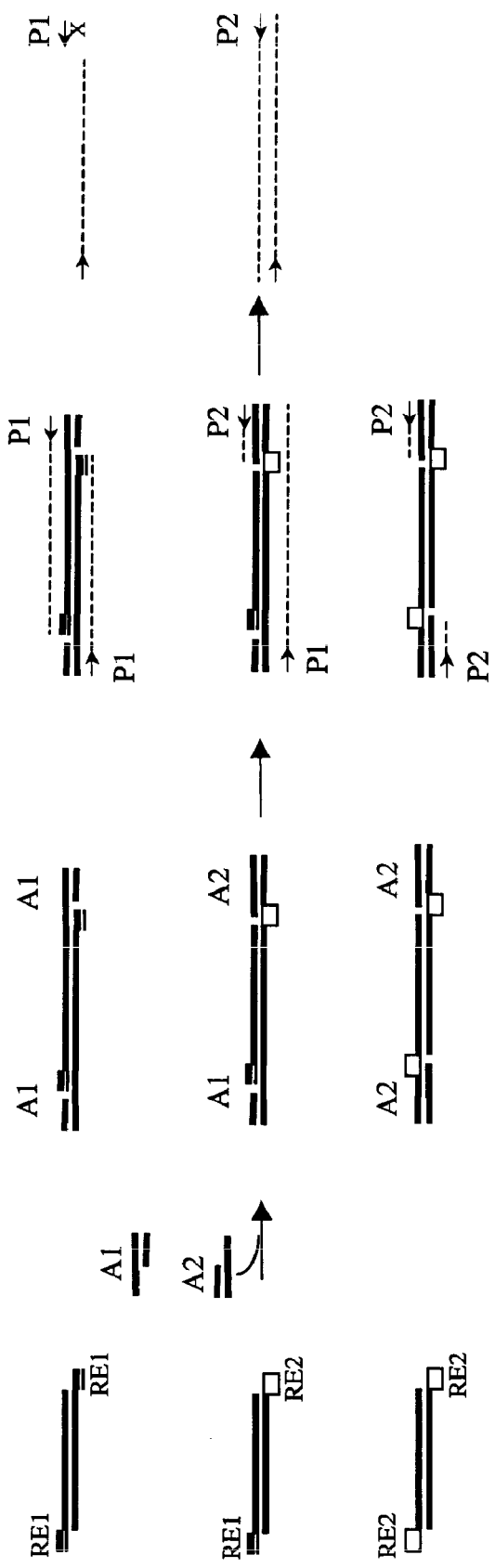
FIG. 2 is a schematic showing how blocked ligation can be used to selectively amplify the fragments that have been digested by two different restriction enzymes.

In this embodiment, the gaps or nicks may be introduced, for example, by blocking ligation of one strand of the adaptor to the fragment. Both the adaptors and the fragments are double stranded so ligation of the adaptor to the fragment typically results in the formation of two phosphodiester bonds, one between one adaptor strand and one strand of the fragment and a second between the other adaptor strand and the other strand of the fragment. In one embodiment of the current invention, formation of one of these phosphodiester bonds is blocked. The adaptor is ligated to the fragment through one phosphodiester bond but one strand of the resulting ligated fragment will have a gap between the adaptor and the restriction fragment. When this strand is used as a template for primer extension the primer extension reaction will stop when the nick or gap is reached as illustrated in FIG. 2.

Ligation of one strand of the adaptor can be selectively blocked by any available method. In a preferred embodiment of the current invention, the adaptors carry a terminal modification that blocks ligation. For example, the presence of a ddNTP at the 3' end of an adaptor strand prevents ligation because there is no 3' hydroxyl available for the ligation reaction. Other 3' modifications that can be used to block ligation include a 3' phosphate group, phosphorothioate, biotin, fluorescent dye, 2',3' cyclic phosphate, or any other modification that results in the absence of a free 3' hydroxyl. Similarly, the absence of a free phosphate at the 5' end of an adaptor strand will block ligation. Typically oligonucleotides are synthesized without a 5' phosphate, but a phosphate can be added by, for example, a kinasing reaction or be removed by, for example, a phosphatase reaction.

Figure 3:
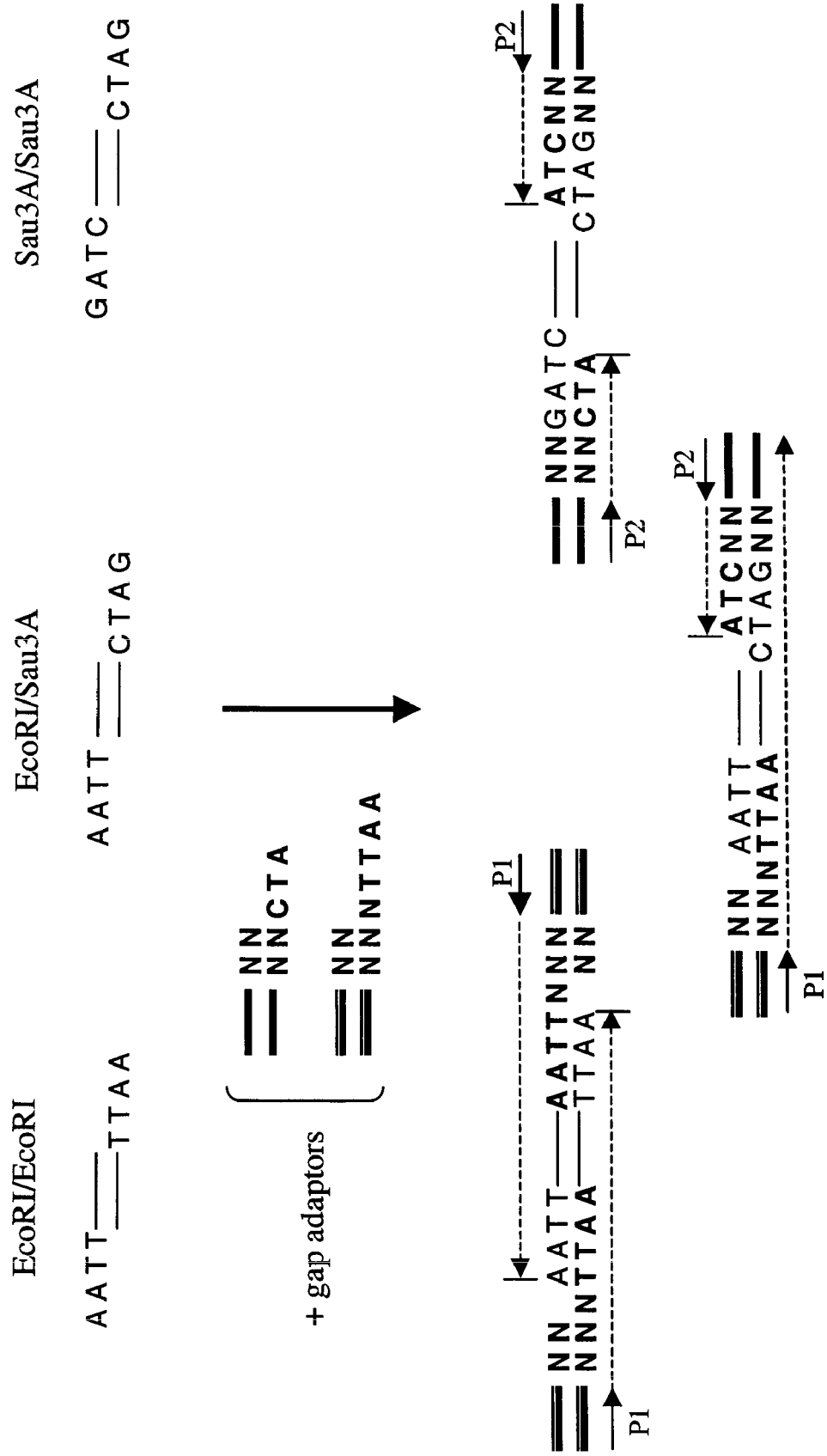
FIG. 3 shows an example of how an adaptor can be used to introduce a gap, resulting in blocked ligation and blocked extension at the gap.

In another preferred embodiment, the adaptors are designed to introduce a gap that blocks ligation. (See, FIG. 3). A gap of one or more bases can be introduced between one strand of the adaptor and one strand of the fragment. One method of introducing such a gap is by designing the adaptor overhang with either one extra base or with one fewer base. (See, FIG. 3). In the example in FIG. 3, the adapter designed to hybridize to the overhang left by Sau3A is designed to introduce a gap between the 5' phosphate of the adaptor and the 3'OH of the fragment (5 '-ATC-3 ' instead of 5 '-GATC-3'). Alternatively, the adaptor designed to hybridize to the overhang left by EcoRI in FIG. 3 will introduce a gap between the 5' phosphate of the fragment and the 3' OH of the adaptor by adding an extra nucleotide to the overhang, (5'-AATTN-3' instead of 5'-AATT-3' where N is any nucleotide).

A combination of methods may also be used, for example, ligation of one adaptor may be blocked by the absence of the necessary phosphate while ligation of the other adaptor is blocked by introduction of a gap of one or more nucleotides.

In this embodiment of the current invention, ligation is preferably blocked at the 5' end of one of the two adaptors and at the 3' end of the other adaptor. More specifically, if ligation of the first adaptor is blocked between the 3' end of the adaptor and the 5' end of the fragment, then ligation of the second adaptor should be blocked between the 5' end of the adaptor and the 3' end of the fragment. Likewise, if ligation of the first adaptor is blocked between the 5' end of the adaptor and the 3' end of the fragment, then ligation of the second adaptor should be blocked between the 3' end of the adaptor and the 5' end of the fragment. As illustrated in FIG. 2, this results in blocked amplification of the fragments with two similar ends but allows for amplification of the fragments with different ends because only those fragments will have a complete template strand.

Figure 4:
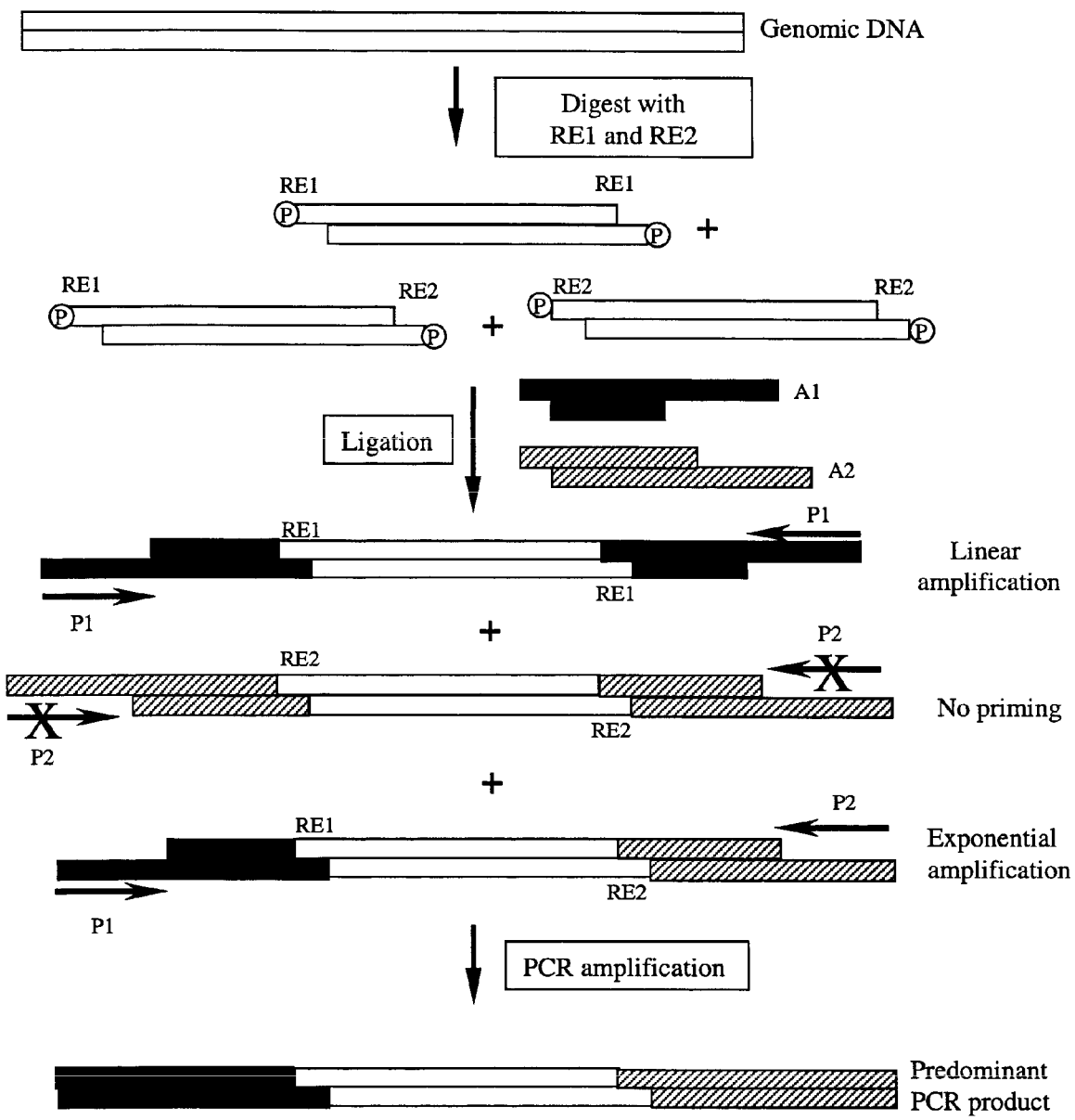
FIG. 4 is a schematic illustration of a method of complexity reduction that uses targeted amplification of a subset of restriction fragments wherein the targeting is accomplished by adding overhangs to the adaptors, which comprise primer binding sites.

In another embodiment of the current invention, illustrated in FIG. 4, the adaptors are designed with single stranded regions that allow for selective amplification. In the example illustrated in FIG. 4, adaptor A1, which is designed to ligate to the overhang left by RE1, has an additional single stranded 3' overhang that serves as a primer binding site for primer P1. Adaptor A2, which is designed to be ligated to the overhang left by RE2, has an additional single stranded 5' overhang that serves as a template for a primer binding site for primer P2. Only fragments that have A1 ligated to one end and A2 ligated to the other end will be amplified. (See FIG. 4).

Using the current invention different combinations of enzymes can be used for digestion based upon the predicted frequency of cutting and the desired level of complexity reduction. For example, using a simplistic theoretical calculation, if a 6 base cutter is combined with a four base cutter the resulting complexity reduction is 8 fold. The 6 base cutter is predicted to cut the genome into fragments that are on average $4^6$ base pairs and the 4 base cutter is predicted to cut the genome into fragments that are on average $4^4$ base pairs. In the double digest, the $4^6$ base pair fragments should be digested into 16 $4^4$ base pair fragments. Two of these fragments, or $\frac{1}{8}^{th}$ of the genome, should have been cut by the 6 base cutter on one end and the 4 base cutter on the other end. In a further example, if an eight base cutter is combined with a four base cutter the complexity reduction is 128 fold. (See, Table 1 below). Similar calculations can be done for enzymes with different length recognition sequences.

In yet another embodiment, further complexity reduction is achieved by designing at least one of the primers to hybridize at its 3' end to at least one nucleotide of the variable region of the restriction fragments to be amplified. The additional selective nucleotide(s) further reduces the complexity of the resulting DNA pool because only those fragments which contain the complement of the specific nucleotide(s) incorporated in the PCR primer will be amplified. The level of complexity in the isolated pool can be varied depending upon the identity and number of nucleotides incorporated into the PCR primers and the restriction enzymes used to fragment the DNA. For example, if an enzyme with a 6 base recognition sequence is combined with an enzyme with a four base pair recognition sequence and only fragments that were digested with both enzymes are amplified on average 1 of every 8 restriction fragments will be amplified. This results in an 8 fold reduction in the complexity of the sample, reducing the 3,300 Mb human genome to 375 Mb. If an additional selective nucleotide is added to one of the primers only $\frac{1}{4}^{th}$ of those fragments will be amplified or 1 out of every 32 restriction fragments, resulting in a 32 fold reduction in complexity. See, Table 1 and Table 2. Different combinations of selective nucleotides can be used to amplify different populations of SNPs. Table 2 illustrates the use of different selective nucleotides in combination with digestion with enzymes with a 6 and 4 base pair recognition sequence. A number of embodiments of the present invention involve amplification by PCR. Any of these embodiments may be further modified to reduce complexity using the above disclosed technique.

TABLE 1

| # of Selective Nucleotides | Number of bases in RE1 recognition site | Number of bases in RE2 recognition site | Fraction of RE1-RE2 Fragments | Complexity Reduction from Total Genome (Mb) |
|---|---|---|---|---|
| 0 | 6 | 4 | 1/8 | 375 |
| 1 | 6 | 4 | 1/32 | 96 |
| 2 | 6 | 4 | 1/128 | 24 |
| 3 | 6 | 4 | 1/512 | 6 |
| 0 | 8 | 4 | 1/128 | 24 |
| 1 | 8 | 4 | 1/512 | 6 |

TABLE 2

| Selective nucleotides | Estimated Complexity | # of TSC SNPs Selected |
|---|---|---|
| 0\|A | 96 Mb | 24,000 |
| A\|A | 24 Mb | 6,000 |
| A\|T | 24 Mb | 6,000 |
| T\|A | 24 Mb | 6,000 |
| C\|T | 24 Mb | 6,000 |
| A\|AT | 6 Mb | 1,000 |
| A\|AG | 6 Mb | 1,000 |

There are many known methods of amplifying nucleic acid sequences including e.g., PCR. See, e.g., *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification. Standard protocols may be found in, for example Sambrook et al. which is hereby incorporated by reference for all purposes.

The DNA polymerase used in PCR is often a thermostable polymerase. This allows the enzyme to continue functioning after repeated cycles of heating necessary to denature the double stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent® (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

As those of skill in the art will appreciate, after isolation and amplification, the resulting sequences may be further analyzed using any known method including sequencing, HPLC, hybridization analysis, etc.

Any of the above embodiments can be combined with in silico digestion techniques to predict the number and identities of SNPs predicted to be represented in a PCR product amplified using the above methods. For example, if restriction fragments that have been cleaved by EcoRI at one end and Sau3A at the other end are the subset to be amplified, a computer can be used to model an EcoRI and Sau3A digest of the genome to identify that subset of fragments and to identify the known or suspected SNPs that are present on that subset of fragments.

The invention also includes kits for performing one or more of the different methods for analyzing a polynucleotide population described herein. Kits generally contain reagents necessary to perform the subject methods. The reagents may be supplied in pre-measured amounts for individual assays so as to increase reproducibility. Reagents may also be provided in a concentrated form.

In one embodiment, the subject kits comprise adaptors and primers to amplify representative restriction fragments. The kits of the invention may also include one or more additional reagents required for various embodiments of the subject methods. Such additional reagents include, but are not limited to: restriction enzymes, DNA polymerases, DNA ligases, buffers, nucleotides and the like.

Methods of Use

The methods of the presently claimed invention can be used for a wide variety of applications. Any analysis of genomic DNA may be benefited by a reproducible method of complexity management. Furthermore, the methods and enriched fragments of the presently claimed invention are particularly well suited for study and characterization of extremely large regions of genomic DNA.

In a preferred embodiment, the methods of the presently claimed invention are used for SNP discovery and to genotype individuals. For example, any of the procedures described above, alone or in combination, could be used to isolate the SNPs present in one or more specific regions of genomic DNA. Selection probes could be designed and manufactured to be used in combination with the methods of the invention to amplify only those fragments containing regions of interest, for example a region known to contain a SNP. Arrays could be designed and manufactured on a large scale basis to interrogate only those fragments containing the regions of interest. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, co-pending U.S. application Ser. Nos. 08/813,159 and 09/428,350 which are herein incorporated by reference in their entirety for all purposes).

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000-2,000 bases when two human chromosomes are compared. (See, The International SNP Map Working Group, Science 409: 928-933 (2001) incorporated herein by reference in its entirety for all purposes.) Human diversity is limited not only by the number of SNPs occurring in the genome but further by the observation that specific combinations of alleles are found at closely linked sites.

Correlation of individual polymorphisms or groups of polymorphisms with phenotypic characteristics is a valuable tool in the effort to identify DNA variation that contributes to population variation in phenotypic traits. Phenotypic traits include physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. *Science* 286: 531-537 (2001) hereby incorporated by reference in its entirety for all purposes.)

Pharmacogenomics

Pharmacogenomics refers to the study of how your genes affect your response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, *Science* 286: 487-491 (2001) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population, prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharmaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures. Paternity testing is commonly used to establish a biological relationship between a child and the putative father of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. *Nature Genet.* 22, 78 (1999)).

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual.

Marker Assisted Breeding

Genetic markers can assist breeders in the understanding, selecting and managing of the genetic complexity of animals and plants. Agriculture industry, for example, has a great deal of incentive to try to produce crops with desirable traits (high yield, disease resistance, taste, smell, color, texture, etc.) as consumer demand increases and expectations change. However, many traits, even when the molecular mechanisms are known, are too difficult or costly to monitor during production. Readily detectable polymorphisms which are in close physical proximity to the desired genes can be used as a proxy to determine whether the desired trait is present or not in a particular organism. This provides for an efficient screening tool which can accelerate the selective breeding process.

Example

Step 1. Restriction Enzyme Digestion of Genomic DNA

2 μg human genomic DNA was digested with 20 units of EcoR I (New England Biolabs) and 20 units of Sau3A I in 80 μl 1×NEB buffer 4 with 1×BSA (NEB) by 37° C. overnight incubation. The enzymes were inactivated at 65° C. for 20 minute.

Step 2. Adaptor Ligation 500 ng genomic DNA digested in step 1 was ligated to 30 μmol EcoR I adaptors (5'-AGTATAAGGGGTTCG-3' (SEQ ID NO 1) and 5'-phosphate-AATTACGAACCCCTTATACT-3' (SEQ ID NO 2)), which leaves a 1 nucleotide gap between the 3' adaptor and the restriction fragment, and 300 μmol Sau3A I adaptors (5'-ATCGCCTTATAGTGAGTCG-3' (SEQ ID NO 3) and 5'-CGACTCACTATAAGGC-3' (SEQ ID NO 4)), which leaves a 1 nucleotide gap between the 5' end of the adaptor and the restriction fragment, with 4000 units of T4 Ligase (NEB) in 1×T4 Ligase buffer (NEB) at 16° C. for overnight. The ligase was inactivated by incubation at 65° C. for 10 minutes.

Because the adaptors were designed to leave a gap in one strand (see FIG. 3), only fragments that were cleaved by both enzymes will ligate both the EcoR I and Sau3AI adaptor sequences to the same strand and be amplified in the following step.

Step 3. Amplification with PCR 4 ng genomic DNA ligated in step 2 was amplified with 2 units AmpliTaq Gold polymerase (PE) and 3 mM EcoR I primer (5'-AGTATAAGGGGTTCGTAATTCA-3'(SEQ ID NO 5)) and 3 mM Sau3A I primer (5'-ACTCACTATAAG-GCGATCA-3'(SEQ ID NO 6)) in 50 μl 1×PCR buffer II (PE) with 2.5 mM $MgCl_2$. PCR was performed in a MJ Research thermal cycler (Watertown, Mass.) with 35 cycles of 94° C. for 30 seconds, 48° C. for 30 seconds and 72° C. for 2 minutes. 400 μl PCR reactions were pooled and purified and quantified by measuring their UV absorbance at 260 nm.

Step 4. Fragmentation, Biotin Labeling and Hybridization to Arrays

5 μg purified PCR product was digested in 40 μl 1× One-Phor-All buffer (Pharmacia) with 0.6 unit DNase I (Promega) at 37° C. for 15 minutes. The DNase I was inactivated by boiling for 15 minutes. 2 μl biotin-N6-ddATP (1.0 mM, NEN) and 3 ul rTDT (15 U/μl, GIBCO) were added to the DNA solution. The DNA fragments were labeled with biotin by incubation at 37° C. for 1.5 hrs. Boiling for 15 minutes inactivated the enzyme. 20 μg DNA was pooled, concentrated, mixed with hybridization cocktail and hybridized to arrays on a rotisserie at 49° C. overnight.

Step 5. Array Washing, Staining and Scanning

Arrays were washed with 6×SSPE buffer on a fluidics station (Affymetrix) and 0.1×MES buffer (Affymetrix) at 45° C. for 30 minutes, stained and scanned under standard procedures.

CONCLUSION

From the foregoing it can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

I claim:

1. A method of determining the bases present at nucleotide polymorphisms in a population of individuals comprising:
providing each of first nucleic acid samples from each of the individuals;
providing each of second nucleic acid samples comprising fragments, from said each of the first nucleic acid samples by: fragmenting said each of the first nucleic acid samples using a first restriction enzyme and a second restriction enzyme, wherein the polymorphisms are predicted to be on fragments that are cut on their one end by the first restriction enzyme and on their other end by the second restriction enzyme; and wherein the polymorphisms are single nucleotide polymorphisms (SNPs) and the fragments that are cut on their one end by the first restriction enzyme and on their other end by the second restriction enzyme are from said second nucleic acid samples;
producing adaptor-ligated fragments by ligating a first and a second adaptor to the fragments from said each of said second nucleic acid samples, wherein the first adaptor has a single stranded 3' region comprising a first primer region and the complement of said first primer region is not present in said first adaptor, and the second adaptor has a single stranded 5' region comprising a second primer region and the complement of said second primer region is not present in said second adaptor, and wherein the first adaptor ligates to the fragments having an end generated by the first restriction enzyme and the second adaptor ligates to the fragments having an end generated by the second restriction enzyme; and wherein adaptor-ligated fragments comprise overhangs having the first primer region and/or overhangs having the second primer region;
amplifying the adaptor-ligated fragments using a first primer complementary to said first primer region and a second primer comprising said second primer region and producing amplified fragments, wherein the amplified fragments generated from the adaptor-ligated fragments that contain both the first adaptor and the second adaptor are enriched in the amplified fragments relative to the amplified fragments generated from the adaptor-ligated fragments that contain the first adaptor and do not contain the second adaptor, and relative to the amplified fragments generated from the adaptor-ligated fragments that contain the second adaptor and do not contain the first adaptor;

providing a plurality of identical nucleic acid arrays consisting essentially of probes designed to detect the bases present at a plurality of polymorphisms predicted to be present in the second nucleic acid samples;

hybridizing said amplified fragments to the plurality of identical nucleic acid arrays;

generating a plurality of hybridization patterns resulting from the hybridizing step; and analyzing the hybridization patterns thereby determining the bases present at the polymorphisms in the population of individuals.

2. The method of claim 1 wherein the SNPs are associated with the efficacy of a drug.

* * * * *

SEQUENCE LISTING

```
<160> NUMBER OF SEQ ID NOS: 6

<210> SEQ ID NO 1
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 1
agtataaggg gttcg                                                    15

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 2
```

```
aattacgaac cccttatact                                              20

<210> SEQ ID NO 3
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 3
atcgccttat agtgagtcg                                               19

<210> SEQ ID NO 4
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 4
cgactcacta taaggc                                                  16

<210> SEQ ID NO 5
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 5
agtataaggg gttcgtaatt ca                                           22

<210> SEQ ID NO 6
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 6
actcactata aggcgatca                                               19
```